US010984935B2

(12) United States Patent
Zheng et al.

(10) Patent No.: US 10,984,935 B2
(45) Date of Patent: Apr. 20, 2021

(54) SUPERCONDUCTING DIPOLE MAGNET STRUCTURE FOR PARTICLE DEFLECTION

(71) Applicant: Hefei Institutes of Physical Science, Chinese Academy of Sciences, Anhui (CN)

(72) Inventors: Jinxing Zheng, Anhui (CN); Yuntao Song, Anhui (CN); Kun Lu, Anhui (CN); Junsheng Zhang, Anhui (CN); Jing Wei, Anhui (CN); Ming Li, Anhui (CN); Feng Jiang, Anhui (CN); Xianhu Zeng, Anhui (CN)

(73) Assignee: Hefei Institutes of Physical Science, Chinese Academy of Sciences, Hefei (CN)

( * ) Notice: Subject to any disclaimer, the term of this patent is extended or adjusted under 35 U.S.C. 154(b) by 0 days.

(21) Appl. No.: 15/557,938

(22) PCT Filed: May 2, 2017

(86) PCT No.: PCT/CN2017/082727
§ 371 (c)(1),
(2) Date: Sep. 13, 2017

(87) PCT Pub. No.: WO2018/201279
PCT Pub. Date: Nov. 8, 2018

(65) Prior Publication Data
US 2020/0058424 A1    Feb. 20, 2020

(51) Int. Cl.
*H01F 1/00*    (2006.01)
*H01F 6/06*    (2006.01)
(Continued)

(52) U.S. Cl.
CPC ............. *H01F 6/06* (2013.01); *A61N 5/1077* (2013.01); *H05H 7/04* (2013.01); *H05H 13/005* (2013.01);
(Continued)

(58) Field of Classification Search
CPC ..... H01F 6/06; H01F 7/00; H01F 7/22; H01F 1/00; H05H 13/04; H05H 13/005; H05H 7/04; A61N 5/1077
(Continued)

(56) References Cited

U.S. PATENT DOCUMENTS 4,680,565 A * 7/1987 Jahnke .................. H05H 7/04
                                                                315/501
4,737,727 A * 4/1988 Yamada .................. H01F 6/00
                                                                313/62
(Continued)

FOREIGN PATENT DOCUMENTS

CN    101307862 A    11/2008
CN    102360692 A    2/2012
(Continued)

OTHER PUBLICATIONS

Yin-Feng, Zhu, "Design and heat load analysisof support structure of CR superconducting dipole magnet forFAIR", Nuclear Fusion and Plasma Physicsvol. 28, No. 3, (Sep. 2008), 5 pgs.
(Continued)

*Primary Examiner* — Shawki S Ismail
*Assistant Examiner* — Lisa N Homza
(74) *Attorney, Agent, or Firm* — Schwegman Lundberg & Woessner, P.A.

(57) ABSTRACT

A superconducting dipole magnet structure that includes coil boxes, a dewar and a support device is provided, wherein each of the coil boxes is of a one-piece structure in which a superconducting coil is provided, wherein the superconduct-
(Continued)

ing coils are opposite to each other so that a uniform dipole magnetic field is generated when the two superconducting coils are energized, and wherein the support device is fixed to the dewar and supports the coil box in the way of point contact.

20 Claims, 6 Drawing Sheets

(51) Int. Cl.
A61N 5/10 (2006.01)
H05H 7/04 (2006.01)
H05H 13/00 (2006.01)

(52) U.S. Cl.
CPC .............. A61N 2005/1087 (2013.01); H05H 2007/046 (2013.01)

(58) Field of Classification Search
USPC ........................................................ 335/216
See application file for complete search history.

(56) References Cited

U.S. PATENT DOCUMENTS

| | | | | |
|---|---|---|---|---|
| 4,902,993 A * | 2/1990 | Krevet | .................. | G21K 1/093 335/210 |
| 5,111,173 A * | 5/1992 | Matsuda | .................. | H05H 7/04 315/503 |
| 5,117,194 A * | 5/1992 | Nakanishi | ................ | H05H 7/04 315/503 |
| 5,182,914 A * | 2/1993 | Barclay | .................. | F25B 21/00 505/889 |
| 5,278,380 A * | 1/1994 | Lowry | .................. | H02H 7/001 219/635 |
| 5,483,129 A * | 1/1996 | Yamamoto | .............. | H05H 7/04 250/396 R |
| 5,946,568 A * | 8/1999 | Hsiao | ................ | H01L 21/76897 257/E21.012 |
| 7,728,311 B2 * | 6/2010 | Gall | ........................ | H05H 13/04 250/492.21 |
| 7,812,319 B2 * | 10/2010 | Diehl | ..................... | G21K 1/093 250/396 ML |
| 8,791,656 B1 * | 7/2014 | Zwart | .................... | H05H 13/02 315/503 |
| 8,933,650 B2 * | 1/2015 | O'Neal, III | .............. | H03L 7/00 315/502 |
| 9,155,186 B2 * | 10/2015 | Zwart | ..................... | H05H 7/04 |
| 9,622,335 B2 * | 4/2017 | Gall | .......................... | H05H 7/04 |
| 9,661,736 B2 * | 5/2017 | O'Neal, III | ............ | H05H 13/02 |
| 10,258,810 B2 * | 4/2019 | Zwart | ..................... | A61N 5/10 |
| 10,646,728 B2 * | 5/2020 | Zwart | ................... | A61N 5/1044 |
| 2002/0195973 A1 * | 12/2002 | Hu | ......................... | H02M 1/126 315/276 |
| 2014/0371076 A1 | 12/2014 | Jongen | | |

FOREIGN PATENT DOCUMENTS

| | | |
|---|---|---|
| CN | 103106994 A | 5/2013 |
| CN | 103177841 A | 6/2013 |
| CN | 105070458 A | 11/2015 |

OTHER PUBLICATIONS

"International Application Serial No. PCT2017082727 International Written Opinion dated Aug. 2, 2018", (Aug. 2, 2018), 6 pgs.
"International Application Serial No. PCT2017082727 International Search Report dated Aug. 2, 2018", (Aug. 2, 2018), 6 pgs.

* cited by examiner

SUPERCONDUCTING DIPOLE MAGNET STRUCTURE FOR PARTICLE DEFLECTION

PRIORITY APPLICATIONS

This application is a U.S. National Stage Filing under 35 U.S.C. 371 from International Application No. PCT/CN2017/082727, filed on 2 May 2017, and published as WO/2018/201279 on Nov. 8, 2018; which application and publication are incorporated herein by reference in its entirety.

TECHNICAL FIELD

The present disclosure relates to a field of superconducting magnets, and particularly to a superconducting dipole magnet structure for particle deflection.

BACKGROUND

The medical technology of particle beam was developed from the United States in 1946 when Wilson firstly proposed particle beam treatment characteristics. There is a Bragg peak in particle beam. The Bragg peak can be adjusted to a tumor area through high-precision computer control technology, and large amounts of energy can be released. With the development of the medical technology of particle beam for half a century, particle therapy becomes a remarkable high and new technology for treatment of cancer because of its penetrating power, good dose distribution, less side scattering and other characteristics. With the continuous development of particle medical technology, heavy ion medical technology is also being developed continuously. In terms of beam type, heavy ions, especially carbon ions, are preferable because of their physical Bragg effect and special relative biological effect.

To achieve the particle and heavy ion medical treatment, the corresponding medical devices are needed. Considering the principle of structural composition, heavy ion and particle therapy systems are substantially the same, including accelerators, particle transport system, nozzle and treatment planning system. And with the rapid development of accelerator science, it has been difficult for conventional magnet accelerators to meet the requirements of various disciplines for high energy particle beam. Due to the high requirements of heavy ion and particle transporting for magnetic rigidity, the magnetic rigidity for deflecting heavy ion is 6.3 T·m and that for proton is 2.15 T·m, which makes it difficult to design the magnet used in the particle beam transport process because of the difficulty of achieving high strength magnetic field with traditional magnet. The only way for this is to increase the size of the magnet to meet the requirements, which makes the size and weight of existing transport system huge. As it is difficult for the conventional magnet to achieve electromagnetic field of high strength, the only way for this is to increase the radius of curvature to meet the requirements, which makes the existing gantry system huge and heavy. Especially for the last bending magnet, the weight of 90 degree bending magnet increases rapidly as the radius thereof increases. Taking Germany GSI HIT as an example, the weight of the 90-degree bending magnet is up to 90 tons, accounting for 65% of the weight of the entire gantry system. Excessive gantry weight will lead to severe deformation due to the uneven stress, thus affecting the isocentric error and rotation accuracy, hindering the wide application of ion beam medical treatment. The bending magnet is an important component of rotating gantry to realize the deflection function of iron beam and is an important factor for the size and weight of rotary gantry. Therefore, it is necessary to change the magnet structure and develop new magnet so as to overcome the defects of existing gantry of large size, high weight and high cost.

SUMMARY

According to an aspect of the present disclosure, there is provided a superconducting dipole magnet structure which includes two coil boxes, a dewar and a support device, wherein each of the coil boxes is of a one-piece structure in which a superconducting coil is provided, the superconducting coils are opposite to each other so that a uniform dipole magnetic field is generated when the two superconducting coils are energized, and wherein the support device is fixed to the dewar and supports the coil box in the way of point contact.

According to another aspect of the present disclosure, a transport device is provided for transporting particles and/or heavy ions, including:

any of the above-described superconducting dipole magnet structures that is provided on the preset transport path of particles and/or heavy ions to achieve deflection of the particle beam.

DETAILED DESCRIPTION OF PREFERRED EMBODIMENTS

Figure 1:
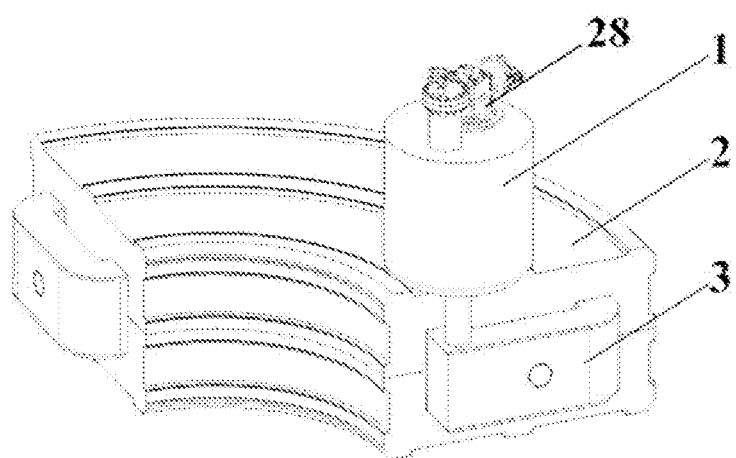
FIG. 1 is a schematic view of the superconducting dipole magnet structure according to the present disclosure.

The disclosure will now be described with reference to the drawings and the embodiments to provide a thorough understanding on the purpose, the technical solution and the advantages of the present disclosure.

According to an aspect of the present disclosure, there is provided a superconducting dipole magnet structure which includes two coil boxes, a dewar and a support device, wherein each of the coil boxes is of a one-piece structure in which a superconducting coil is provided, the superconducting coils are opposite to each other so that a uniform dipole magnetic field is generated when the two superconducting coils are energized, and wherein the support device is fixed to the dewar and supports the coil box in the way of point contact.

Further, the point contact is achieved such that the support device supports the coil box by means of pins, wherein the support device includes a main support, and the pins are provided on the main support, and wherein an end surface of the pin is directly opposite to the coil box.

Further, the support device fixes and supports the coil box by means of bolts, and the main support and the coil are riveted by means of bolts.

Further, the periphery of the bolts and pins between the support device and the coil box is provided with a heat insulating member to reduce the heat transfer between the support device and the coil box, and heat insulation from outside is achieved.

Further, the superconducting dipole magnet structure includes a dewar and two thermal shields, wherein the thermal shields are arranged at the periphery of the coil boxes and vacuum is formed therebetween, wherein the dewar is arranged outside the thermal shields and vacuum is formed therebetween, and wherein the superconducting dipole magnet structure further comprises a liquid cold source that is provided by means of a refrigerator to provide a constant temperature.

Further, the thermal shield is supported by the support device, and a heat insulating member is provided on a portion of the support device supporting the thermal shield.

Further, the superconducting dipole magnet structure further includes a heat insulating plate in which a through hole is formed, the main support of the support device passes through the hole and a portion of the support device is supported by the heat insulating plate, and the dewar indirectly supports the support device embedded in the heat insulating plate by supporting the end of the heat insulating plate.

Further, a elongated circuit is provided between the heat insulating plate and the main support to reduce the heat leakage, and a convex structure is provided on the wall of the through hole.

According to another aspect of the present disclosure, a transport device is provided for transporting particles and/or heavy ions, including:

any of the above-described superconducting dipole magnet structures that is provided on the preset transport path of particles and/or heavy ions to achieve deflection of the particle beam.

According to another aspect of the present disclosure, a medical device is provided which includes a particle accelerator, a therapeutic device, and a transport device described above, wherein the transport device for the particle is disposed at downstream of the accelerator and at upstream of the therapeutic device, so that the particles and/or heavy ions accelerated by the accelerator can be transported to the therapeutic device.

According to the above-described technical solution, it is possible to obtain the following advantageous effects of the present disclosure:

1. The special support device can meet the structural strength requirements while ensuring the achievement of reducing heat transfer;
2. The support device can achieve connection and positioning between the coil box and the thermal shield by means of the bolts and the pins;
3. The periphery of the support device is wrapped with heat insulating members (such as G10 ring) to reduce the heat transfer between the coil box and the thermal shield; the structural connection and the reduction of heat transfer between the thermal shield and the dewar are also achieved by the similar structure; the housing of the dewar is made of stainless steel and is internally vacuumized; finally, the beam stream deflecting function of the coil is achieved under a working condition of a low temperature of 4K;
4. The superconducting magnet structure based on superconducting material (such as NbTi) can effectively increase the magnetic field in the effective region of the dipole magnet while realizing the particle beam deflection function, and realize small, lightweight and cheap development of particle beam transport system, which plays an important role in technical development and extensive use of particle beam therapy;
5. The medical device of the present disclosure mainly adopts the structure design of superconducting dipole magnet of the accelerator technology, achieving functions of high current stable operation, magnet cooling in the liquid helium temperature region, quench protection, steady magnetic field with high strength, and so on.

In the present disclosure, the term "point contact" means that the coil box and the support device are contacted by way of one or more points on the face, where the point may be circular, oval in shape, or be of other planar shape. The purpose of doing this is to reduce the contact area as much as possible so as to reduce the heat transfer between the coil box and the support device. The above "contact" may be achieved by a variety of ways, including but not limited to other support structures, such as supporting posts of heat insulating material (G10 epoxy material) provided on the support device which is fixed to the coil box.

The basic concept of the present disclosure is to propose a superconducting dipole magnet structure suitable for accelerator technology, which includes a support device with a specific structure. The superconducting dipole magnet structure greatly increases carrying current density of the coil while ensuring the strength of the magnet structure.

Figure 4:
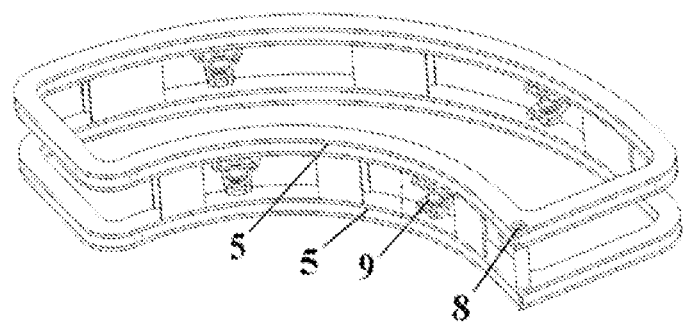
FIG. 4 is a schematic view of the support device and the coil box in FIG. 1.

FIG. 1 is a schematic view of the superconducting dipole magnet structure according to the present disclosure, and FIG. 4 is a schematic view of the support device and the coil box in FIG. 1. Referring to FIG. 1 and FIG. 4, the superconducting dipole magnet structure includes coil boxes 5 and a supporting device 9, wherein each of the coil box 5 is of a one-piece structure in which a superconducting coil is provided, the superconducting coils are opposite to each other (including the upper coil 19 and the lower coil 20 when the coils are directly opposite in the vertical direction) so that a magnetic field is generated when the two superconducting coils are energized, and wherein the support device 9 supports the coil box 5 in the way of point contact.

The superconducting dipole magnet structure is an important component in the particle and/or heavy ion transport device. The role of the transport device is to ensure an unobstructed transport of the particle beam in the vacuum pipe. The transport device mainly includes the main transport system and a rotary gantry, wherein the gantry includes the superconducting dipole magnet structure.

FIG. 1 is that the superconducting dipole magnet structure is of an arc-shaped structure as a whole, and the angle of the arc-shaped structure corresponds to the angle by which the particles will be deflected. An arc-shaped beam stream vacuum pipe 4 is arranged inside the arc-shaped structure, the entrance and exit thereof are arranged on two sides of the superconducting dipole magnet structure, the particles pass through the superconducting dipole magnet structure from one side to the other side, achieving the angle deflection. The superconducting dipole magnetic structure may include a superconducting magnet cooling system 1 and a superconducting magnet coil system 3. The superconducting magnet cooling system 1 is used to maintain a constant operating temperature of superconducting coil and the superconducting magnet coil system 3 is used for producing a stable electromagnetic field.

Figure 2:
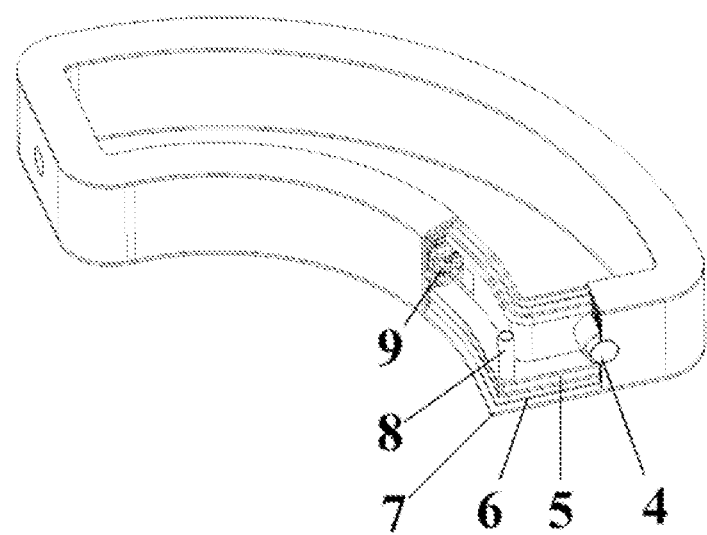
FIG. 2 is a schematic view of a partial section of the superconducting dipole magnet in FIG. 1.
Figure 3:
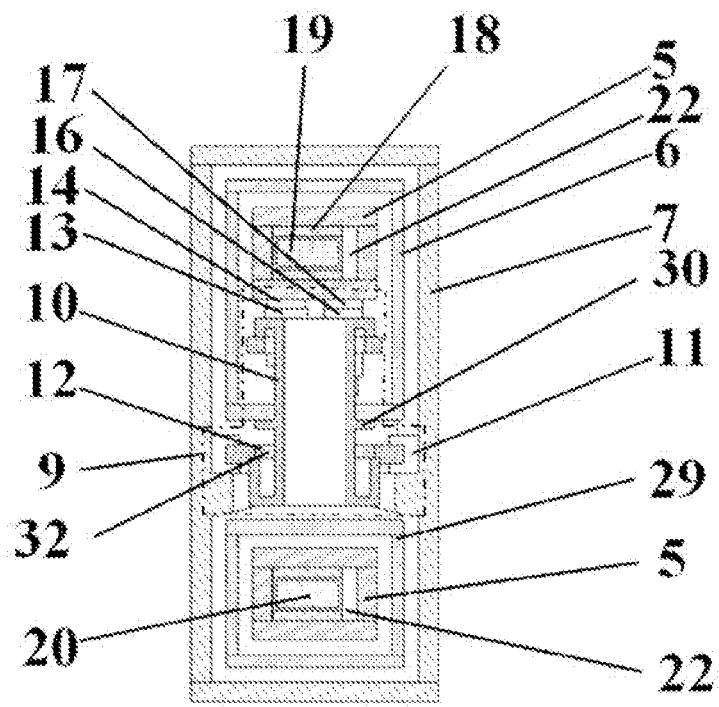
FIG. 3 is a cross-sectional view of the superconducting dipole magnet in FIG. 1.
Figure 12:
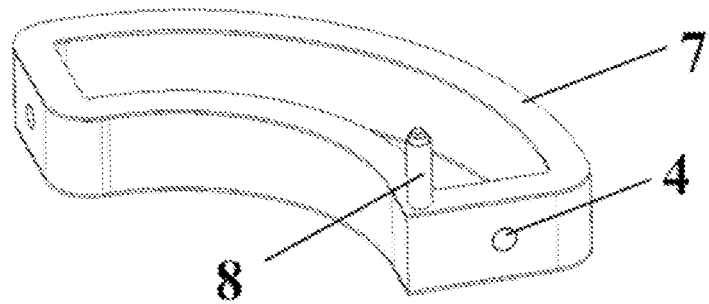
FIG. 12 is a schematic view of the dewar in FIG. 1.
Figure 13:
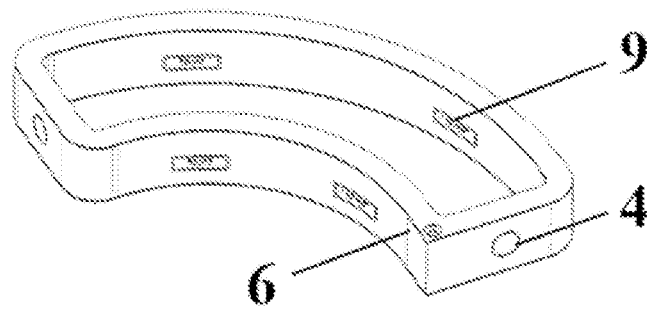
FIG. 13 is a schematic view of the cold screen thermal shield in Figure. 1.

FIG. 2 is a schematic view of a partial section of the superconducting dipole magnet in FIG. 1; and FIG. 3 is a cross-sectional view of the superconducting dipole magnet in FIG. 1. As shown in FIG. 2 and FIG. 3, the superconducting magnet coil system 3 may include the cold screen 6, the dewar 7 and the cooling pipe 8. The support device 9 is supported on the dewar 7 with a heat insulating member 11 and a heat insulating plate 12 therebetween. As shown in FIG. 12 and FIG. 13, the housing of the dewar 7 is made of stainless steel, and the dewar is vacuumized. Finally, a beam stream deflection function of the superconducting magnet is achieved when the internal superconducting coils are energized under a condition of a low temperature of 4K. The cold screen 6 is made of copper, located between the dewar and the coil boxes, is in a vacuum environment, and is fixed by the support device. The dewar 7 is mainly used to provide a vacuum environment, achieving a vacuum heat insulating effect. The cold screen 6 mainly plays a role of reducing thermal radiation.

FIG. 4 is a schematic view of the support device and the coil boxes in FIG. 1. The support device 9 is used to support the coil box 5 (including the components inside the coil boxes). In order to reduce the influence of the support device 9 on the temperature inside the coil box 5, the contact area between the support device 9 and the coil box 5 should be as low as possible. By the point contact way, the corresponding contact area can be reduced, thereby improving the heat insulating coefficient. In addition, a heat insulating member can be placed at the contact portion to further improve the heat insulating effect.

In some embodiments, the coil box 5 may be supported by means of bolts and pins in a point contact manner to achieve the coupling and positioning between the coil box and the thermal shield. The support device supports the coil box 5 (which is provided with an opening for receiving the pins) by means of the pins 14. The support device 9 includes a main support 10, wherein the pins are provided on the main support 10 and the ends of pins is directly opposite to the coil box. The support device 9 further fixes and supports the coil box by bolts 17, and the main support and the coil box are riveted by means of bolts. Riveting by bolt means that the bolt is screwed into the threaded hole in one of the two parts to be connected so as to connect the two parts together.

In some embodiments, the bolts 17 and the pins 14 at the top of the support structure are wrapped with heat insulating members (13, 16) (e.g., G10 rings) to reduce the thermal conductivity between the coil box and the main support.

In some embodiments, the coil box 5, the thermal shield 6 and the dewar 7 are independent of each other and can only be connected through the support device.

In a preferable embodiment, the thermal shield 6 is supported by the support device 9, and a heat insulating member is provided between the support device 9 and the thermal shield 6.

Figure 5:
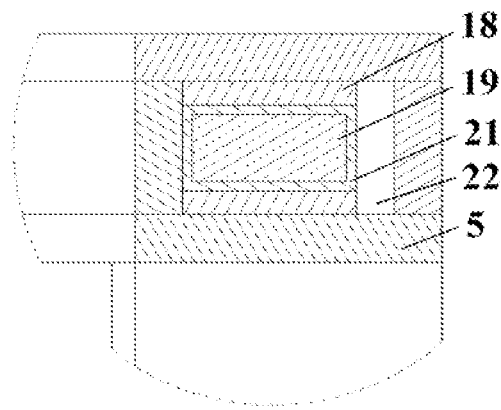
FIG. 5 is a cross-sectional view of the coil box in FIG. 1.

FIG. 5 is a cross-sectional view of the coil boxes in FIG. 1. Each of the coil boxes 5 is of a one-piece structure in which a relatively closed space is formed to facilitate the transport of the particles and to improve the uniformity of the cross-section and the uniformity of the integral magnetic field in the good field area in the beam stream aperture.

Opposite coils are provided inside the coil boxes. The coils can be divided into an upper coil 19 or a lower coil 20 if the two coils are vertically opposite. The upper coil 19 and the lower coil 20 are connected in series to the external circuit and the current flows through them in a same direction. Then a unidirectional uniform dipole magnetic field is generated in the magnet gap. The upper coil 19 and the lower coil 20 are used to generate a magnetic field with a certain strength to deflect the particle beam after being energized. A coil body electrical insulating member 21 and a cooling channel 22 is provided outside the coils.

Figure 6:
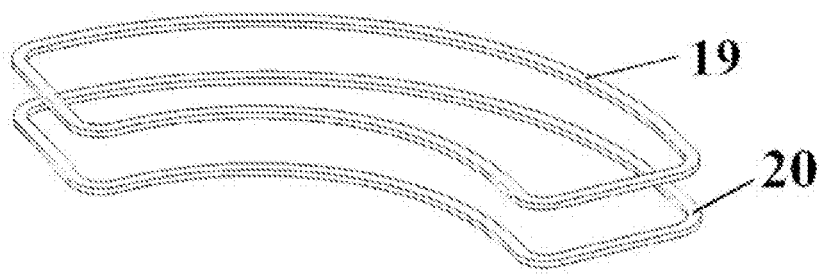
FIG. 6 is a schematic view of the superconducting coil in FIG. 1.
Figure 7:
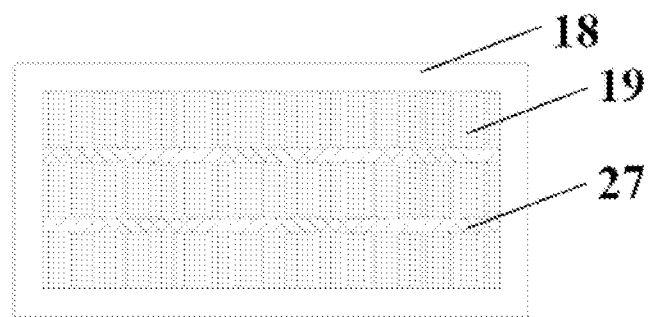
FIG. 7 is a cross-sectional view of the superconducting coil in FIG. 1.

FIG. 6 is a schematic view of the superconducting coil in FIG. 1; and FIG. 7 is a cross-sectional view of the superconducting coil in FIG. 1. Referring to FIG. 6 and FIG. 7, the upper coil 19 and the lower coil 20 are made of high-temperature superconducting material, (Such as YBCO) or low-temperature superconducting material (such as NbTi). Since the large size and the heavy weight of the conventional magnet, the performance of the magnet is restricted. The superconducting material can improve the field strength of the dipole magnet so that the bending radius of the magnet is effectively reduced and the overall length of the gantry is then reduced. Thus, the whole structure is more compact, the load on the gantry can be reduced to ensure stable transmission of the beam stream. There are coil layer electrical insulating members 27 between respective turns of the upper coil 19.

Figure 8:
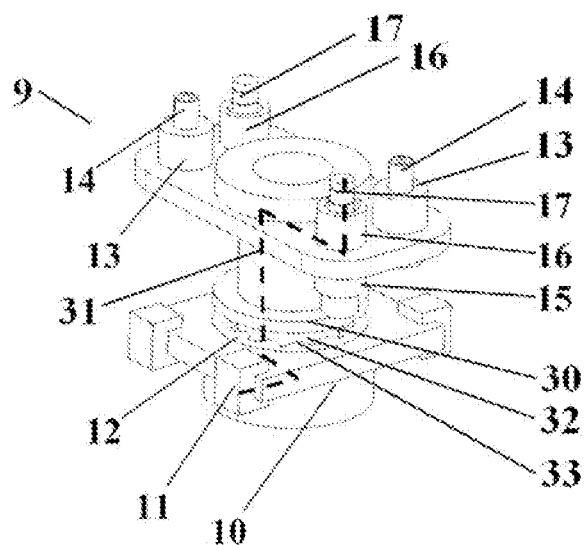
FIG. 8 is a perspective view of the support device in FIG. 1.
Figure 9:
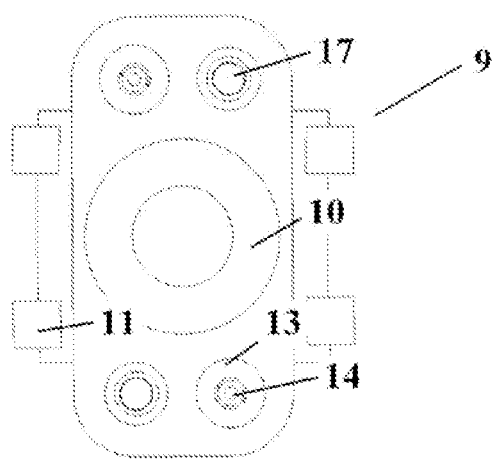
FIG. 9 is a top view of the support device in FIG. 1.
Figure 10:
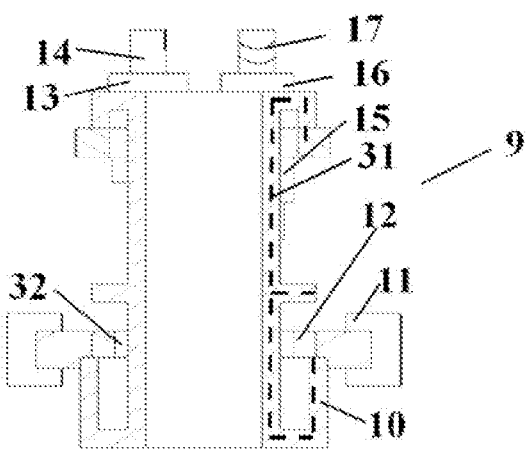
FIG. 10 is a cross-sectional view of the support device in FIG. 1.

FIG. 8 is a perspective view of the support device in FIG. 1; FIG. 9 is a top view of the support device in FIG. 1; and FIG. 10 is a cross-sectional view of the support device in FIG. 1. Referring to FIGS. 8-10, the support device according to the present embodiment mainly includes a main support 10 and a heat insulating member 30. The heat insulating member 30 supports the thermal shield 6. The coil box 5 is connected and supported by the main support 10 through the bolts 17 and the pins 14 at the upper part of the main support 10. The pins 14 are used to realize radial positioning and the bolts 17 are used for fixing, realizing axial positioning. The main support 10 is also used to support the cold screen 6 provided outside the coil box 5. The contact manner between the cold screen 6 and the main support 10 is different from that between the coil box 5 and the main support 10, so that there is no direct contact between the coil box 5 and the cold screen 6.

As is shown in Figure 8, the support device 9 further includes a heat insulating plate 12 (e.g., a G10 plate) in which a through hole 32 is provided. The main support 10 passes through the through hole 32 and is supported by the heat insulating plate 12. The dewar 7 indirectly supports the main support 10 embedded in the heat insulating plate by supporting the end of the heat insulating plate 12.

Preferably, a heat insulating member 11 (e.g., G10 block) is provided on the heat insulating plate 12 where the heat insulating plate 12 is in contact with the dewar 7, further improving the heat insulation effect.

Preferably, in order to increase the strength of the coupling structure consisting of the heat insulating plate 12 and the main support 10 and to reduce the contact area therebetween, as shown in FIG. 8, a convex structure 33 including a plurality of protrusions is provided at the periphery of the central opening of the heat insulating plate.

It is further preferred that an elongated circuit 32 is formed between the main support 10 and the heat insulating plate 12 to increase the length of the heat conduction path.

The heat transfer circuit is shown in FIG. 10 with a thick dash line. The elongated circuit 31 is realized with curved shape of main support 10.

Figure 11:
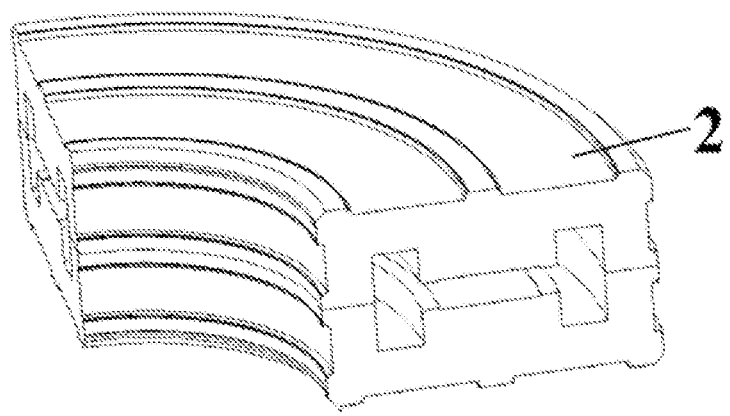
FIG. 11 is a schematic view of the iron yoke in FIG. 1.

In some embodiments, the superconducting dipole magnet structure further includes an iron yoke 2, as shown in FIG. 1 and FIG. 11, which are substantially H-typed. The iron yoke 2 consists two symmetrical portions and are assembled of half structures. The superconducting coil system is provided inside the iron yoke 2, and the outer surface of the dewar 7 is fitted and fixed to the inside of the iron yoke 2, and the iron yoke 2 is mainly used to increase the field strength and to improve the magnetic field uniformity.

Figure 14:
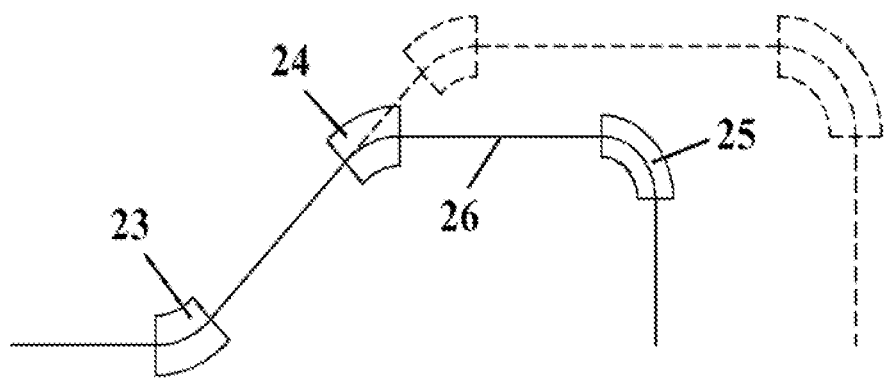
FIG. 14 is a layout of beam transport device according to the present disclosure.

FIG. 14 is a schematic diagram showing a layout of a transport device according to an embodiment of the present disclosure. The present disclosure also provides a transport device for transporting particles and/or heavy ions. The transport device includes a plurality of dipole magnet structures, at least one of which adopts the superconducting dipole magnet structure as described above. Each of the superconducting dipole magnet structures is placed in preset transmission path for particles/heavy ions to achieve deflection of the particle beam. According to one embodiment, a 60-degree dipole magnet 23 in FIG. 14 first deflects the ion beam from the axis, and then other two superconducting dipole magnet structures (a 60-degree dipole magnet 24 and a 90-degree dipole magnet 25) or more superconducting dipole magnet structures (indicated by the dashed lines in FIG. 14) reversely deflect them in the beam stream vacuum pipe 26 so that the beam stream is perpendicular to the rotation axis of the rotary gantry.

The present disclosure further provides a medical device which includes a particle accelerator, a transport device for particle described above and a therapeutic device, wherein the transport device for the particle is disposed at downstream of the accelerator and at upstream of the therapeutic device, so that the particles and/or heavy ions accelerated by the accelerator can be transported to the therapeutic device. The superconducting magnet is different from a conventional magnet which requires a large water supply and purification system, and the superconducting magnet is of light weight, small size, high stability, uniformity, and low energy consumption. The characteristics of high field strength and high stability of superconducting magnet can rotate the gantry for proton treatment. With such an arrangement, the weight of the gantry can be greatly reduced due to the 90 degree dipole magnet at the end of path of particle according to the present disclosure. Therefore, such design will be the key to the application development of ion beam therapy technology, and there is great significance in promotion for the application of the superconducting technology in the field of medical physics development.

With the above-described embodiments of the present disclosure, the above-mentioned special cooling and support device ensures a low-temperature cooling effect of the magnet and a high-strength and steady-state uniform magnetic field, thereby finally achieving the deflection of the particle beam. At the same time, the special structural features thereof can effectively reduce the size, weight and cost of the magnet, and ensure the safe release of the current in the magnet in the failure such as quench.

The objects, technical solutions and advantages of the present disclosure has been described in the foregoing detailed description. It will be understood that the above description only relates to particular embodiments according to the present disclosure and is not intended to limit the present disclosure and that any modifications, equivalents, improvements within the spirit and principles of the present disclosure are intended to be included within the scope of the present disclosure.

The invention claimed is:

1. A superconducting dipole magnet structure that comprises two coil boxes, a dewar and a support device,
    wherein each of the coil boxes is of a one-piece structure in which a superconducting coil is provided,
    wherein the superconducting coils are opposite to each other so that a uniform dipole magnetic field is generated when the two superconducting coils are energized, and
    wherein the support device is fixed to the dewar and supports the coil box in the way of point contact.

2. The superconducting dipole magnet structure according to claim 1,
    wherein the point contact is achieved such that the support device supports the coil box by means of pins,
    wherein the support device comprises a main support, and the pins are provided on the main support, and
    wherein an end surface of each of the pins is directly opposite to the coil box.

3. The superconducting dipole magnet structure according to claim 2,
    wherein the support device fixes and supports the coil box by means of bolts, and the main support and the coil box are connected by means of bolts.

4. The superconducting dipole magnet structure according to claim 3,
    wherein the periphery of the bolts and pins between the support device and the coil box is provided with a heat insulating member to reduce the heat transfer between the support device and the coil box, and heat insulation from outside is achieved.

5. The superconducting dipole magnet structure according to claim 2,
    wherein the superconducting dipole magnet structure further comprises a heat insulating plate in which a through hole is formed, the main support of the support device passes through the hole and a portion of the support device is supported by the heat insulating plate, and the dewar indirectly supports the support device embedded in the heat insulating plate by supporting the end of the heat insulating plate.

6. The superconducting dipole magnet structure according to claim 5,
    wherein an elongated circuit is formed between the heat insulating plate and the main support to reduce the heat leakage, and a convex structure is provided on the wall of the through hole.

7. The superconducting dipole magnet structure according to claim 1,
    wherein the superconducting dipole magnet structure further comprises a dewar and two thermal shields,
    wherein the thermal shields are arranged at the periphery of the coil boxes and vacuum is formed therebetween, and
    wherein the dewar is arranged outside the thermal shields and vacuum is formed therebetween.

8. The superconducting dipole magnet structure according to claim 7,
    wherein the thermal shield is supported by the support device, and a heat insulating member is provided on a portion of the support device supporting the thermal shield.

9. A transport device for transporting particles and/or heavy ions, comprising:

the superconducting dipole magnet structures according to claim 1 that is provided on a preset transport path of particles and/or heavy ions to achieve deflection of the particle beam.

10. A medical device, characteristics comprising:
a particle accelerator, a therapeutic device, and a transport device according to claim 9,
wherein the transport device for the particle is disposed at downstream of the accelerator and at upstream of the therapeutic device, so that the particles and/or heavy ions accelerated by the accelerator are transported to the therapeutic device.

11. The medical device according to claim 10,
wherein the point contact is achieved such that the support device supports the coil box by means of pins,
wherein the support device comprises a main support, and the pins are provided on the main support, and
wherein an end surface each of the pin is directly opposite to the coil box.

12. The medical device according to claim 11,
wherein the support device fixes and supports the coil box by means of bolts, and the main support and the coil box are connected by means of bolts.

13. The medical device according to claim 10,
wherein each of a periphery of a portion of each bolt that is disposed between the support device and the coil box and a periphery of each pin that is disposed between the support device and the coil box is provided with a heat insulating member to reduce the heat transfer between the support device and the coil box, and heat insulation from outside is achieved.

14. The transport device according to claim 9,
wherein the point contact is achieved such that the support device supports the coil box by means of pins,
wherein the support device comprises a main support, and the pins are provided on the main support, and
wherein an end surface of each of the pins is directly opposite to the coil box.

15. The transport device according to claim 14,
wherein the support device fixes and supports the coil box by means of bolts, and the main support and the coil box are connected by means of bolts.

16. The transport device according to claim 15,
wherein the periphery of the bolts and pins between the support device and the coil box is provided with a heat insulating member to reduce the heat transfer between the support device and the coil box, and heat insulation from outside is achieved.

17. The transport device according to claim 14,
wherein the superconducting dipole magnet structure further comprises a heat insulating plate in which a through hole is formed, the main support of the support device passes through the hole and a portion of the support device is supported by the heat insulating plate, and the dewar indirectly supports the support device embedded in the heat insulating plate by supporting the end of the heat insulating plate.

18. The transport device according to claim 17,
wherein an elongated circuit is formed between the heat insulating plate and the main support to reduce the heat leakage, and a convex structure is provided on the wall of the through hole.

19. The transport device according to claim 9,
wherein the superconducting dipole magnet structure further comprises a dewar and two thermal shields, wherein the thermal shields are arranged at the periphery of the coil boxes and vacuum is formed therebetween, and
wherein the dewar is arranged outside the thermal shields and vacuum is formed therebetween.

20. The transport device according to claim 19,
wherein the thermal shield is supported by the support device, and a heat insulating member is provided on a portion of the support device supporting the thermal shield.

* * * * *